United States Patent

Illum

[19]

[11] Patent Number: 5,935,604
[45] Date of Patent: Aug. 10, 1999

[54] NASAL DRUG DELIVERY COMPOSITION CONTAINING NICOTINE

[75] Inventor: Lisbeth Illum, The Park, United Kingdom

[73] Assignee: Danbiosyst UK Limited, Nottingham, United Kingdom

[21] Appl. No.: 08/553,401

[22] PCT Filed: May 20, 1994

[86] PCT No.: PCT/GB94/01092

§ 371 Date: Jul. 1, 1996

§ 102(e) Date: Jul. 1, 1996

[87] PCT Pub. No.: WO94/27576

PCT Pub. Date: Dec. 8, 1994

[30] Foreign Application Priority Data

May 20, 1993 [GB] United Kingdom .................. 9310412

[51] Int. Cl.⁶ ..................... A61K 31/33; A61K 31/465
[52] U.S. Cl. ............... 424/501; 424/78.14; 424/483; 424/499
[58] Field of Search ................... 424/438, 440, 424/78.1, 437, 78.14; 514/813

[56] References Cited

U.S. PATENT DOCUMENTS

| | | |
|---|---|---|
| 2,945,783 | 7/1960 | Beekman et al. . |
| 3,655,866 | 4/1972 | Bilotti . |
| 4,655,231 | 4/1987 | Ray et al. . |
| 4,882,152 | 11/1989 | Yang et al. . |
| 4,971,787 | 11/1990 | Cherukuri et al. . |
| 5,525,351 | 6/1996 | Dam .................... 424/440 |
| 5,599,554 | 2/1997 | Prajeti .................. 424/448 |
| 5,603,943 | 2/1997 | Yanagawa ............. 424/434 |
| 5,656,255 | 8/1997 | Jones .................... 424/434 |

FOREIGN PATENT DOCUMENTS

| | | |
|---|---|---|
| 0107941 | 5/1984 | European Pat. Off. . |
| 0166440 | 1/1986 | European Pat. Off. . |
| 0286085 | 10/1988 | European Pat. Off. . |
| 0338861 | 10/1989 | European Pat. Off. . |
| 3545090 | 6/1987 | Germany . |
| 3914170 | 11/1990 | Germany . |
| 4140116 | 6/1993 | Germany . |
| 2033915 | 5/1980 | United Kingdom . |
| 2 133 691 | 5/1986 | United Kingdom . |
| WO 91/09599 | 7/1991 | WIPO . |
| 93/10797 | 6/1993 | WIPO . |
| 95/05165 | 2/1995 | WIPO . |

OTHER PUBLICATIONS

Anonymous, Research Disclosure No. 23915 (Mar. 1984).

Benowitz, "Nicotine Replacement Therapy: what has been accomplished—can we do better?," Drugs 45(2): 157–70 (1993).

Benowitz, "Toxicity of Nicotine" in *Nicotine Replacement: a Critical Evaluation* (Pomerleau & Pomerleau. eds.) pp. 204–209 (1992).

(List continued on next page.)

*Primary Examiner*—Peter F. Kulkosky
*Attorney, Agent, or Firm*—Arnall Golden & Gregory, LLP

[57] ABSTRACT

The present invention provides a nasal drug delivery composition comprising nicotine or a pharmacologically-acceptable salt or derivative thereof wherein the composition is adapted to delivery a pulse of nicotine for rapid absorption and a controlled release of nicotine for subsequent sustained absorption. The controlled release phase can be achieved by providing an ion-exchange material which will form a complex with the nicotine. The ion-exchange material may be a polymeric material such as a polysaccharide, or may be in the form of bioadhesive ion-exchange microspheres. The pulse release can be achieved by overloading the ion-exchange material with nicotine so that the composition contains some excess nicotine for immediate release and absorption. Alternatively, some nicotine may be associated with a non ion-exchange material which will release the nicotine immediately on contact with the nasal mucosa, for example non-ion-exchange bioadhesive microspheres.

18 Claims, 2 Drawing Sheets

OTHER PUBLICATIONS

Christen & McDonald, "Safety of Nicotine Gum" in *Nicotine Replacement: a Critical Evaluation* (Pomerleau & Pomerleau. eds.) pp. 220–221 (1992).

Herrmann, et al., "Nicotine Absorption after Pulmonary Instillation," *J. Pharmaceutical Sciences* 81(11):1055–58 (1992).

Hughes, "Dependence Potential and Abuse Litigation" in *Nicotine Replacement: a Critical Evaluation* (Pomerleau & Pomerleau. eds.) pp. 272–75 (1992).

Illum, et al., "Bioadhesive Microspheres as a Potential Nasal Drug Delivery System," *Int. J. Pharm.*, 39:189–199 (1987).

Jarvis, et al., "Nasal Nicotine Solution as an Aid to Cigarette Withdrawal: a pilot clinical trial," *British Journal of Addiction*, 82:983–88 (1987).

Johansson, et al., "Absolute bioavailabilty of nicotine applied to different nasal regions," *Eur. J. Clin. Pharmacol.* 41:585–88 (1991).

Olsson, et al., "Pharmacokinetics of Nicotine After Intranasal Administration," *Effects of Nicotine on Biological Systems, Advances in Pharmacological Sciences*, pp. 57–61 (Birkhäuser Verlag Basel 1986).

Pomerleau, et al., "Controlled dosing of nicotine via Intranasal Nicotine Aerosol Delivery Device (INADD)," *Psychopharmacology* 108:519–26 (1992).

Russell, "Blood Nicotine Levels" in *Nicotine Replacement: a Critical Evaluation* (Pomerleau & Pomerleau. eds.) pp. 74–93 (1992).

Russell, et al., "Nasal nicotine solution: a potential aid to giving up smoking?," *British Med. Journal*, 286:683–85 (1983).

West, "Nicotine Dependence" in *Nicotine Replacement: a Critical Evaluation* (Pomerleau & Pomerleau. eds.) pp. 238–255 (1992).

Walter Rahn, Pharmazeutische Zeitung, pp. 2214–2218 (1982).

Römp Chemie Lexikon, 9th Edition, p. 200 (1989).

NASAL DRUG DELIVERY COMPOSITION CONTAINING NICOTINE

The present invention relates to compositions for nasal administration and, more particularly, to compositions for nasal administration of nicotine.

Smoking remains the single most important preventable cause of death in modern society. It can be estimated that in the US alone more than 430,000 deaths in 1988 were attributable to cigarette smoking. At least nine out of ten smokers are to some extend dependent upon nicotine and 75% are moderately to strongly dependent and continue smoking despite attempts to stop. In the United States the strong interest in stopping smoking is demonstrated by the fact that nearly 20 million people try to quit smoking each year. Their need for additional help can be seen in the fact that more than 90% fail to maintain their abstinence.

The major problem with nicotine is that it is highly addictive. Nicotine fulfils all criteria of an addictive drug, it is psychoactive, it affects the mood, it can act as a primary reinforcer, it induces tolerance, and physical as well as psychological changes occur on withdrawal.

Importantly, there is no direct evidence that nicotine itself is carcinogenic or mutagenic, nor does it act as a tumour initiator, promoter or co-carcinogen. Similarly, none of the major metabolites of nicotine are known to be carcinogenic. In contrast, tobacco and especially tobacco smoke contains several potent carcinogens.

A major limiting factor in the successful use of nicotine replacement therapy for smoking cessation is the lack of an appropriate delivery system. When a person smokes a cigarette, the level of nicotine rise rapidly in the blood and in the brain with an interval of just 10–20 seconds between taking a puff and the nicotine arriving in the brain. The presently marketed nicotine replacement products, the transdermal nicotine patch and the nicotine chewing gum, are not entirely satisfactory in that they do not provide the patient with the nicotine "buzz" associated with smoking a cigarette, since they are both slowly acting controlled release systems where only low nicotine plasma levels are obtained. Hence clinical trails have shown that only about 20%–30% of those smokers who have used nicotine patches and nicotine chewing gum successfully quit smoking after one year compared to 15% of those smokers receiving behavioural support alone.

Transdermal patches seem to be no more effective than placebo in maintaining smoking cessation in the long term. The long term results after the use of patches alone have not been impressive. Medical Letter (Vol. 34, 37, 1992).

The nicotine chewing gum is a slow release preparation where the rate of release of nicotine will depend on the rate of chewing. It takes 20–30 min of vigorous chewing to release 95% of the nicotine content of the gum. Without chewing or if the gum is accidently swallowed, negligible amounts of nicotine are released. The gum contains 2 or 4 mg of nicotine. A typical smoker needs about 15 pieces of gum a day. The gum has an unpleasant taste and may be irritating to the mouth and throat. Potential side effects are heartburn and hiccups. Tired and aching jaws may be experienced from intensive chewing and users rarely maintain blood nicotine concentrations above one third of their levels from smoking. The chewing gum is contraindicated in individuals with gastritis or active peptic ulcer disease and presents difficulties for those wearing dentures.

U.S. Pat. Nos. 3,877,468, 3,901,248 and 3,845,217 discloses a chewing gum comprising nicotine in the form of a complex with an insoluble cation-exchange base.

The nicotine patch placed on the skin will give a steady release of nicotine over 24 hours and should be changed daily. The patch is available in three sizes delivering about 21, 14 and 7 mg/24 hours. With the patch in place it takes 3–4 hours to attain significant blood levels of nicotine. The continuous dosing provided by patches can disrupt the usual day/night variation in nicotine intake provided by smoking and can result in a total dose of nicotine per 24 hour exceeding the normal smoking dose. Moreover it seems that if nicotine is given both night and day compared to only daytime, sleep disturbances and nightmares can result. A potential side effect of the patch is skin irritation. A further disadvantage with the nicotine patch is that it is a passive system and for some individuals, a closer involvement with the treatment is to be preferred.

Thus, neither the nicotine patch system nor the nicotine chewing gum system can be considered to be satisfactory for nicotine replacement therapy and smoking cessation.

It is well established that nicotine is easily absorbed nasally. Nicotine concentrations in the blood of regular users of dry snuff are similar to those of cigarette smokers and peak concentrations after a single pinch of snuff is reached in a time similar to that for smoking a cigarette. The absolute bioavailability of nicotine applied to different nasal regions has been measured by Johansson et al., Eur. J. Clin. Pharmacol. 41,585 (1991) in man. Single doses of 1 mg were given and plasma concentrations followed over 6 hours. Bioavailability, as compared to IV infusion was 60 to 75%. The rate of absorption was fast, the maximum concentration being reached within about 10 minutes. No differences could be found for different nasal treatments.

Nasal sprays containing nicotine have been suggested as an alternative approach for smoking cessation. The prior art has described various devices for the better delivery of nicotine. For example WO 87/03813 a spray device with an electronic timer restricting doses to a predetermined number per session is described. A nasal aerosol spray supplying nicotine for anti-smoking therapy is mentioned as an advantage. In U.S. Pat. No. 4,655,231 an improved snuff for nasal application of nicotine containing a pure nicotine salt, a water soluble diluent and colouring and—flavouring is described. The water soluble diluent is preferably an organic acid. The mixture allows rapid application of nicotine. GB 2133691 describes an aqueous solution of nicotine or a non-toxic salt of nicotine together with a non-irritating thickening agent. The composition has a pH of 2–6 and has a viscosity of at least 100 CP. The thickening agent is a natural or synthetic polymer or an oil substance comprising the oil phase of an emulsion. A nicotine solution with a viscosity less than 100 CP has been mentioned in RD 239015. WO 91/09599 discloses a smoking substitute for sublingual administration comprising a nicotine-cyclodextrin complex. The composition is stated to have improved stability and taste, pH independent release and reduced irritant sensation. It is also suggested that the composition could be given nasally.

The nasal nicotine systems discussed above were designed to give rapid absorption of nicotine, followed by a rapid decrease in the level of absorbed nicotine, mimicking the effect of smoking a cigarette. More recently, Sutherland et al. *Lancet* 340,324 (1992), suggested that the rapid absorption of the nicotine when given nasally may be an important factor for smokers for whom other forms of replacements are too slow. Although nasal nicotine spray systems will provide the desired, "buzz" effect, the benefit is short lived and will necessitate frequent dosing. This will be unacceptable to the potential user.

The pharmacokinetics of nicotine in man has been described in some detail (for example see Benowitz, *Ciba Found. Symp.* 152 (1990). The importance of including features associated with tolerance has been stressed. For example, in the end of the day, the response of the cigarette is blunted owing to the development of tolerance. Tolerance can develop and regress in cycles throughout the day. Because of dose response and tolerance characteristics, habitual smokers need to smoke at least 15 cigarettes and consume 20–40 mg of nicotine per day to achieve the desired effect of cigarette smoking and to minimise withdrawal discomfort. The dose of systemically available nicotine absorbed by regular smokers averages about 1 mg per cigarette. The daily nicotine intake of smokers averages about 25 mg. Two minutes after the first cigarette the plasma nicotine level reaches about 13 µg/l. The nicotine peak plasma levels of regular smokers of 15 or more cigarettes per day average about 35 µg/l during daytime.

SUMMARY OF THE INVENTION

An improved nicotine replacement formulation can be achieved by providing a nasal composition which provides both an initial rapid release and absorption of nicotine, a pulse effect, followed by a controlled release and absorption of nicotine to provide a sustained high level of absorbed nicotine. The invention therefore provides a nasal drug delivery composition comprising nicotine or a pharmacologically acceptable salt or derivative thereof in which the nicotine or nicotine salt or derivative is released as a pulse followed by a controlled release phase. The pulse effect provides an initial rapid peak in plasma nicotine levels which gives the "buzz" effect of smoking a cigarette. The controlled release phase then provides a more gradually increased and maintained high plasma level of nicotine, removing the craving for further nicotine, and avoiding the need to use the composition at frequent intervals.

DETAILED DESCRIPTION OF THE INVENTION

Figure 1:
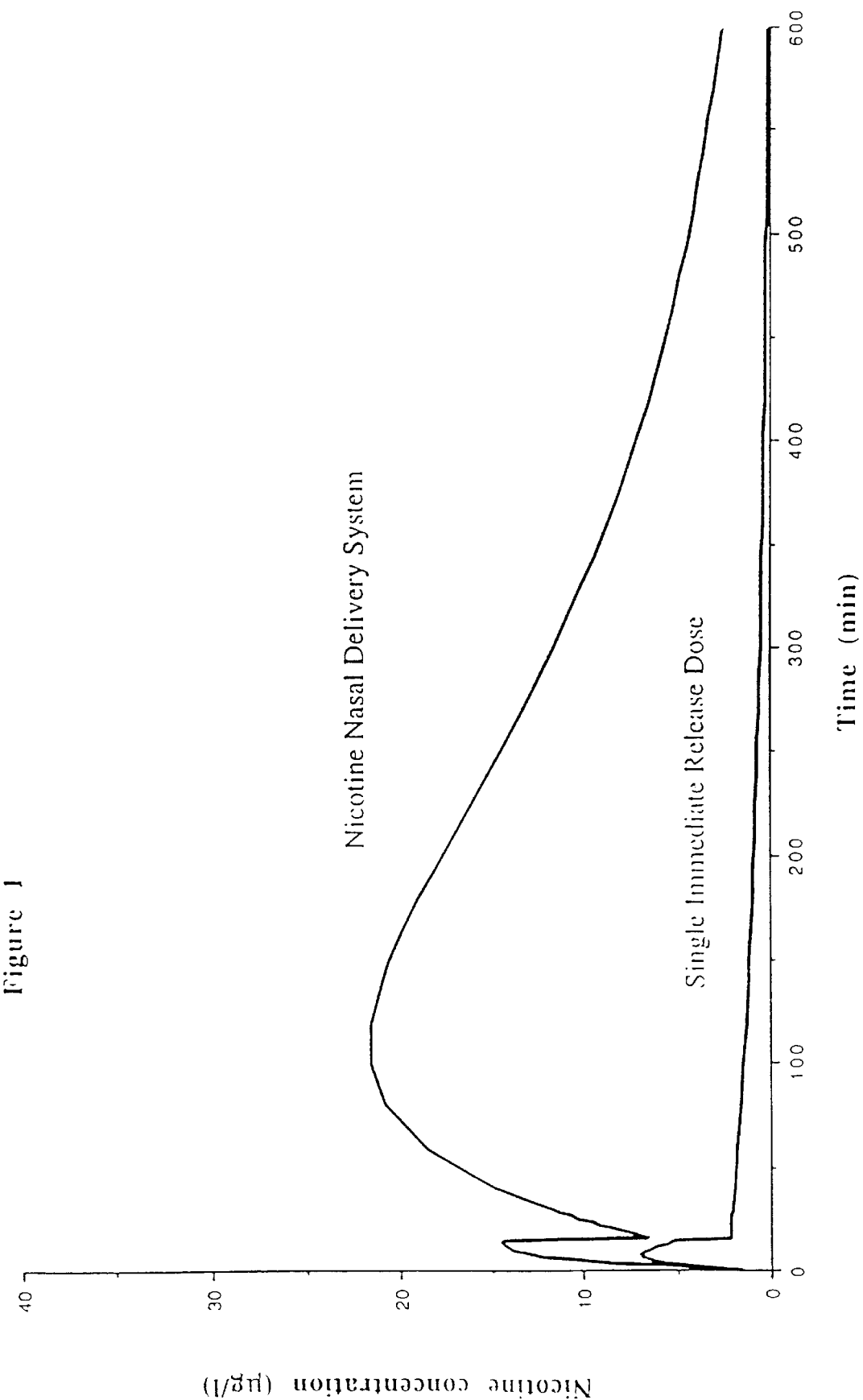
FIG. 1 is a computer generated curve of the time course of nicotine concentration in the body compartment of the model system following intranasal administration of a compound containing 1000 µg alone.

The controlled release effect can be achieved by providing an ion-exchange material in the composition. By-ion-exchange material is meant a natural or synthetic material comprising ionisable groups and which have the ability to exchange ions attracted to their ionised groups with ions of the same charge present in solution. Nicotine is a basic drug and when ionised it carries a positive charge. The ion-exchange material must therefore be one which when ionised releases a positive ion leaving a negative charge to which the ionised nicotine is attracted. The ion-exchange material forms a complex with the ionised nicotine and releases the nicotine slowly when in contact with the nasal mucosa.

The ion-exchange capacity of the ion-exchange material used should preferably be in the range 0.01–50 milli equivalents/g, more preferably 0.1–20 meq/g and most preferably 0.2–10 meq/g.

The ion-exchange material is preferably. bioadhesive to aid its retention in the nasal cavity. By bioadhesive is meant a material which will adhere to the surface of the nasal cavity. The ion-exchange material gradually releases nicotine, providing a controlled release and uptake of nicotine across the nasal mucosa.

Natural or synthetic nicotine may be used or a pharmacologically-acceptable salt or derivative of nicotine. Nicotine forms water soluble salts and double salts with many metals and acids. The use of salt forms of nicotine avoids the problems associated with the free base form of nicotine, including losses due to volatility and decomposition in the presence of oxygen. Preferred salts includes nicotine dihydrogen tartrate, nicotine tartrate, nicotine hydrochloride, nicotine oxalate, nicotine hydrogen tartrate, nicotine dihydrochloride, nicotine sulphate, 2-methyl nicotine and other nicotine derivatives. Nicotine dihydrogen tartrate or nicotine tartrate are especially preferred and also 2-methyl nicotine which has reduced side-effects on the heart. Unless otherwise stated, all amounts of nicotine stated are calculated as the equivalent amount of nicotine free base.

The pulse release of nicotine may be achieved by providing a material which is not an ion-exchange material. The nicotine associated with this material will then be released immediately on contact with the nasal mucosa for rapid absorption. Alternatively, excess nicotine is provided in the composition so that the ion-exchange material is overloaded with nicotine. The excess nicotine not bound by-the ion-exchange material is available for immediate uptake on contact with the nasal mucosa. This excess nicotine is also referred to throughout as "free nicotine".

Monovalent cations can also be included in the composition to compete with the nicotine for binding with the ion-exchange material, thus ensuring that some of the nicotine is left as free nicotine. Such cations should be non-toxic and pharmacologically acceptable, for example sodium, calcium and ammonium.

The ion-exchange material may be in the form of bioadhesive microspheres, or may be an aqueous solution, suspension or freeze-dried preparation of a polymeric material.

It has previously been shown that bioadhesive microspheres are able to increase the residence time of a formulation in the nasal cavity thereby increasing the time available for absorption of the drug (Illum et al, *Int. J. Pharm.* 39,189 (1987).

It was also shown by Illum. et al., *Int. J. Pharm.* 46,261 (1988) that such a system was able to increase the absorption of the antibiotic agent, Gentamicin, thereby allowing it to be given via the nasal route rather than by injection.

The use of the bioadhesive microspheres in drug delivery compositions for transmucosal administration has been described in WO 88/09163 and WO 89/03207.

The slow release of drugs and model compounds from ion-exchange microspheres has been the subject of previous work (Illum and Davis, *Int. J. Pharm.* 11,323. Here the strong binding of the drug to the microspheres via a process of ionic interaction has been used to modify drug release rates. The applications described were for parenteral administration and the local administration of an anionic drug sodium cromoglycate to the nasal cavity. Various ion-exchange microsphere systems are described in the prior art (for example see Kwon, et al., *J. Colloid Interface Sci.* 143, 501 (1991), Kwon, et al., *Int. J. Pharm.* 79, 191 (1992)) Cremers, et al., *J. Controlled Rel.* 11, 167 (1990) and Codde, et al., *Anti-Cancer Res.* 10, 1715–1718 (1990)). None of these systems has been used nasally for nicotine administration.

The ion-exchange microspheres suitable for use in the present invention are microspheres which carry suitable anionic groups such as carboxylic acid residues, carboxymethyl groups, sulphopropyl groups and methylsulphonate groups. Carboxylated starch microspheres are especially preferred. Other materials include hyaluronic acid, chondroitin sulphate, alginate, heparin and heparin-albumin conjugates, as described in Kwon et al. (1991); albumin-poly (α-L glutamic acid), albumin-poly (aspartic acid) or ion-exchange albumin microcapsules as described by Sawaya, et al., *J. Pharm. Sci.* 76, 475 (1987). Ion-exchange resins (cation exchangers) can also be used such as AMINEX-A-6™ (Biorad); a resin containing sulphonate groups or those with carboxymethyl or sulphopropyl groups, Cation exchanges which can be used include carboxymethyl dextran (CM SEPHADEX™) and sulphopropyl dextran (SP SEPHADEX™) carboxymethyl agarose (CM, SEPHAROSE™), carboxymethyl cellulose, cellulose phosphate,, sulphoxyethyl cellulose, agarose (SEPHAROSE), cellulose beads (SEPHACEL) and dextran beads (SEPHADEX) (all available from Pharmacia) are materials which such functional groups. Carboxylated starch microspheres (CADEXOMER) are available from Perstorp.

Cation exchangers on polystyrene include the Amberlite and Dowex strongly acidic cation exchangers and the Amberlite weekly acidic cation exchangers as described in the Sigma Chemical Co Ltd catalogue, 1993, p1591–1593. The Amberlite strongly acidic cation exchangers have sulphonic acid functional groups and the weakly acidic ones have carboxylic acid functional groups. The Dowex exchanger has nuclear sulphonic acid functional groups.

The ion-exchange microspheres can be used with free nicotine to provide both the fast pulse release of nicotine and the controlled release, or can be mixed with non-ion-exchange microsphere. Nicotine is adsorbed to the surface of the non-ion-exchange microsphere and will be released quickly on contact with the nasal mucosa to provide the pulsed effect. Suitable materials for use as non-ion-exchange microspheres include starch, gelatin, collagen and albumin. When a mixture of ion exchange and non-ion-exchange microspheres are used, the composition should contain between 50:1 and 1:1 of ion-exchange-to non-ion-exchange microspheres, preferably 25:1 to 5:1, and more preferably 10:1.

The term microsphere as used herein is defined as substantially spherical particles which can be a monolithic solid sphere or in the form of a small capsule. To ensure correct deposition in the nasal cavity, the microspheres should preferably be of a size between 0.5 and 250 µm more preferably 10–100 µm.

The microspheres can be made by procedures well known in the art, including spray drying, coacervation and emulsification (see for example Davis, et al., *Microsphere and Drug Therapy,* Elsevier, 1984).

EXAMPLE 1

Preparation of Starch Microspheres by an Emulsion Technique 5 g potato starch were dissolved in 95 ml of water at about 90° C. A second solution was prepared from 3 g of polyethylene glycol ($M_w$=6000) and 46 ml of water. This solution was heated to about 70° C., whereafter the warm starch solution was added while stirring, to form an emulsion. When the two-phase system had formed (with the starch solution as the inner phase) the mixture was allowed to cool to room temperature under continued stirring, wherewith the inner phase was converted to gel particles. The particles were filtered off at room temperature and slurried in 100 ml of ethanol, whereafter the particles were again filtered off and laid to dry in air.

The yield was 90%.

EXAMPLE 2

Preparation of Soluble Potato Starch Microspheres by a Coacervation Technique 15 ml 5% starch solution (pH=7) was kept at a constant temperature of 70° C. and stirred (500 rpm) while a 30% solution of polyethylene glycol was added (~7 ml) until phase separation had occurred. The system was stirred for a further 15 min before it was cooled on ice with constant stirring. The microspheres were then isolated by filtration and freeze-dried. With a stirring speed of 500 rpm particles with a mean size of 33 µm±µm were produced.

The ion-exchange microspheres can be made from suitable ion-exchange material which already contains the appropriate functional groups, or non-ion-exchange microspheres of suitable materials can be functionalised by methods well known in the art to provide ion-exchange microspheres.

For the microsphere compositions a nicotine salt should preferably be used to ensure that the nicotine is in its ionised form. The nicotine or nicotine salt is adsorbed to the microspheres by admixing with the microspheres after their formation.

The microspheres, both ion-exchange and non-ion-exchange, can be hardened by well known cross-linking procedures such as heat treatment or by using chemical cross-linking agents. Suitable agents include dialdehydes, including glyoxal, malondialdehyde, succinicaldehyde, adipaldehyde, glutaraldehyde and phthalaldehyde, diketones such as butadione, epichlorohydrin, polyphosphate and borate. Dialdehydes are used to cross-link proteins such as albumin by interaction with amino groups, and diketones form schiff bases with amino groups. Epichlorohydrin activates compounds with nucleophiles such as amino or hydroxyl to an epoxide derivative. The cross-linkers used for the ion-exchange microspheres should not be directed towards the relatively charged groups required for binding the nicotine.

The microsphere composition can be produced as a freeze-dried formulation and administration nasally by the usual methods, for example by using a nasal insufflator. Such devices are well known.

As another alternative embodiment, the composition may comprise solely non-ion-exchange microspheres. In this case the nicotine or nicotine salt is incorporated into the microsphere during its formulation, and this incorporated nicotine will then be released from the microsphere gradually to provide the controlled release effect. Excess nicotine is then mixed with the microspheres after their formulation and adsorbs to the microsphere as before. This nicotine will, as described above, be released from the microsphere immediately on contact with the nasal mucosa to provide the pulse effect.

EXAMPLE 3

Incorporation of Nicotine into a Non-Ion-Exchange Microsphere

Human serum albumin based microspheres containing nicotine were prepared by an emulsification technique; 75 ml of cotton seed oil was mixed with 25 ml of petroleum ether and stirred for 10 min in a 200 ml beaker using a magnetic stirrer. Nicotine was dissolved in the HSA solution (2, 3 or 5% w/v), to obtain drug solution (2%) in aqueous phase. The aqueous phase containing HSA and nicotine was added to the ethereal solution of cotton seed oil dropwise with continuous stirring using a mechanical stirrer at 1000 rpm for 15 min. The microspheres were stabilized by adding 0.1 ml of 25% w/v glutaraldehyde solution with continuous stirring for 15 min or by adding the emulsion system to preheated cotton seed oil (100 ml) at 120° C. dropwise with continuous stirring. The microspheres were separated by centrifugation at 3000×g for 15 min and washed with petroleum ether three times for complete removal of oil adhering to the microsphere surface. The microspheres were filtered using Millipore filter and again washed with petroleum ether and ethanol. Preparations were freeze-dried and stored frozen until used in further studies. For 1 dose, using a 2, 3 or 5% w/v HSA solution, 30, 40 or 50 mg of nicotine containing microspheres were mixed with, for example, 2 mg of nicotine or freeze dried in an aqueous solution containing 2 mg nicotine.

The composition may also be a liquid formulation comprising a polymeric ion-exchange material. The polymeric material should provide a negatively charged group as discussed above and also should provide a viscous solution to aid retention in the nasal cavity. Preferably the material will gel when in contact with the nasal mucosa.

Suitable polymeric materials include gellan gum, welan, rhamsan, alginate, carboxymethylcellulose, sodium alginate, xanthan, agar, guar derivatives such as carboxymethyl guar gum, carageenan, dextran sulphate, keratan, dermatan, pectin. Polysaccharides and derivatives are particularly suitable ("Polysaccharides and derviatives" edited by R C Whistler and J N BeMiller (3rd Ed.) Academic Press, San Diego 1993).

A preferred material is gellan gum, which is the deacetylated form of the extracellular polysaccharide from *Pseudomonas elodae*. Native/high-acyl gellan is composed of a linear sequence of tetra-saccharide repeating units containing D-glucuronopyranosyl, D-glucopyranosyl and L-rhamnopyranosyl units and acyl groups.

Another preferred material is alginate. Alginate is composed of two building blocks of monomeric units, namely β-D-mannuronopyranosyl and α-guluronopyranosyl units. The ratio of D-mannuronic acid and L-guluronic acid components and their sequence predetermines the properties observed for alginates extracted from different seaweed sources.

Welan is produced by an Alealigenes species. Welan has the same basic repeating unit as gellan but with a single glycosyl sidechain substituent. The side unit can be either an α-L-rhamnopyranosyl or an α-L-mannopyranosyl unit linked (1→3) to the 4-0-substituted β-D-glucopyranosyl unit in the backbone.

Rhamsan is produced by an Alcaligenes species. Rhamsan has the same repeating backbone unit as that of gellan but with a disaccharide side chain on 0-6 of the 3-0-substituted β-D-glucopyranosyl unit. The side chain is a β-D-glucopyranosyl-(1-6)-α-D-glucopyranosyl unit.

Xanthan is produced by a number of Xanthomonas strains. The polymer backbone, made up of (1→4)-linked β-D-glucopyranosyl units is identical to that of cellulose. To alternate D-glucosyl units at the 0-3 position, a trisaccharide side chain containing a D-glucoronosyl unit between two D-mannosyl units is attached. The terminal β-D-mannopyranosyl unit is glycosidically linked to the 0-4 position of the β-D-glucopyranosyluronic acid unit, which in turn is glycosidically linked to the 0-2 position of an α-D-mannopyranosyl unit.

Carrageenan is a group of linear galactan polysaccharides extracted from red seaweeds of the Gigartinaceae, Hypneaceae, Solieriaceae, Phyllophoraceae and Furcellanraceae families that have an ester sulfate content of 15–40% and contain alternatively (1→3)-α-D- and (1→4)-α-D-glycosidic linkages.

Agar is a hydrophilic colloid extracted from certain marine algae of the class Rhodophyceae where it occurs as a structural carbohydrate in the cell walls (see also Kang and Pettitt: Xanthan, Gellan, Welan and Rhamsan in Industrial gums by Whistler and BeMiller (Eds), Academic Press Inc. London, 1993).

Mixtures of gellan with other polymers such as alginate can be used, gelling of the mixture being caused by the gellan gum. Other combinations of gums can also be used, particularly where the combination gives a synergistic effect, for example in terms of gelation properties. An example is xanthan—locust bean gum combinations.

The advantage of gellan over other materials is that it can be administered as a fluid system but in the nasal cavity the system will gel, thereby providing a bioadhesive effect and holding the drug at the absorptive surface for an extended period of time.

The grade of gellan gum can be GELRITE™ or KELCO-GEL™ from Kelco Int, Ltd. or other similar grades from other manufacturers. The gellan can be prepared at a concentration of 0.1 w/v to 15% but a preferred range of concentrations is 0.2% to 1%.

For gelling to occur, particularly of gellan gum, monovalent or divalent cations must be present in the composition. Suitable cations include sodium, potassium, magnesium and calcium. The ionic concentration is chosen according to the degree of gelling required, and allowing for the effect that the ionised drug present may have on gelling. At a 0.2% gum concentration, the divalent ions, calcium and magnesium give maximum gel hardness and modulus at molar concentrations approximately one fortieth ($\frac{1}{40}$) of those required with the monovalent ions, sodium and potassium. A finite concentration of each cation is required to induce gelation. For the nasal formulations, the ionic strength is kept sufficiently low to obtain a low viscosity formulation but sufficiently high to ensure gelation once administration into the nasal cavity where gelation will take place due to the presence of cations int he nasal liquid. The ionic strength for a 0.5% gellan gum can be in the range of 0.1 mM–50 mM for monovalent cations, with the preferred range being 1 mM–5 mM and 0.1 mM–5 mM for divalent cations with the preferred range being 0.15 mM–1 mM. For higher concentrations of gellan gum the ionic strengths should be lowered accordingly. The cations will compete with the positively charged nicotine for binding with the polymeric material, and whilst this may be desirable to a certain degree to ensure the presence of free nicotine in the composition, the concentration of cations should be controlled so that sufficient nicotine will bind with the ion-exchange polymeric material.

The complex between nicotine and the ion-exchange material forms as a result of ionic interaction between the negatively charged polymeric material and the positively charged nicotine. The pH of the composition must therefore be such that the two species are fully ionised. The pH should be kept in the range pH 3 to 8, preferably pH 4 to 6, by the presence of appropriate buffers or acids. For these ion-exchange materials the nicotine can be added either as nicotine itself or as a nicotine salt or derivative as the control of the pH by the addition of appropriate acids will ensure that the nicotine is in its ionised form.

The liquid formulations are administered using well-known nasal spray devices. If the formulations are freeze-dried, they can be administered using a nasal insufflator, as for the microsphere preparations.

In a liquid formulation, the polymeric ion-exchange material will typically be provided in a concentration of from 0.01% to 20%, preferably 0.05–10%, more preferably 0.1%–5%.

The compositions can also contain any other pharmacologically-acceptable, non-toxic ingredients such as preservatives, antioxidants, flavourings etc. Benzalkonium chloride may be used as a preservative. However, as this is positively charged, it will compete with the ionised nicotine for binding with the ion-exchange material and can therefore be used to regulate the nicotine binding and ensure the presence of free nicotine for the pulse absorption.

The nicotine or nicotine salt or derivative should be present in an amount to provide a ratio of between 50:1 to 1:1, preferably 25:1 to 2:1, most preferably 15:1 to 5:1 of nicotine bound to the ion-exchange material and free nicotine or nicotine bound to the non-ion exchange material calculated as the equivalent nicotine free base. The amount of nicotine or salt or derivative used will be chosen according to the dose required, but the composition will typically deliver an initial pulse of 0.2 to 3 mg, preferably 1 mg, equivalent nicotine free base for rapid absorption and 5–20 mg, preferably 10 mg equivalent nicotine free base released in a controlled manner for sustained absorption. The composition should preferably deliver the pulse of nicotine for absorption over a period of 30 minutes, preferably 20 minutes and more preferably 10 or 5 minutes after administration. The composition should preferably deliver controlled release of nicotine for absorption over a period of 12 hours, preferably 10 hours and more preferably 6 hours following administration. For a liquid formulation, the concentration of nicotine in the formulation, calculated as the equivalent free base would be 1–20%, preferably 1–10%, more preferably 2–7%. For a freeze-dried powder or microsphere preparation, the concentration would be 1–75%, preferably 2–50%, more preferably 5–25%. The formulations would typically be administered every six hours. However the composition will provide for more extended periods between administration, for example 10 hours, for night time use. Specific embodiments of the invention will now be described in the following examples and with reference to the Figures.

It has been found that an improved nicotine replacement therapy can be achieved by a nasal nicotine composition which provides a two phase release and absorption of nicotine—an initial rapid pulse of nicotine followed by a controlled release phase.

Computer modelling studies have shown the pattern of nicotine levels that will be achieved with such a system. This is shown in FIG. 1. From this it will be seen that the composition provides a nicotine profile which shows an initial sharp peak of nicotine absorption followed by a larger but more gradual and sustained peak. This is in contrast to the sharp but rapidly decreasing peak found with a single immediate release dose of nicotine achieved for example with the currently known nasal nicotine delivery systems or seen when smoking a cigarette.

Specific embodiments are shown in the following examples.

EXAMPLE 4

Preparation of Nicotine-Starch Microspheres

Starch microspheres (ELDEXOMER™) and starch microspheres that carried carboxyl groups (CADEXOMER™) were obtained from Perstorp Fine Chemical Companies, Sweden. The microspheres had a particle size in the range of 53–106 micron diameter in the unswollen state. The microspheres (5 g) at a ratio of 10:1 carboxylated to non-carboxylated were mixed with 20 ml of an aqueous solution of nicotine (pH adjusted to 7) at a concentration of 5%. The system was freeze dried and doses of 50 mg powder were packed into gelatin capsules for administration by a nasal insufflator device. The immediate release component was 1 mg and the controlled release component 9 mg.

EXAMPLE 5

Preparation of Nicotine-Alginate Gum Microspheres

An aqueous solution was prepared containing 25 mg/ml of sodium alginate and 2 mg/mi gellan gum using heating to 70° C. and continuous stirring. Nicotine dihydrogen tartrate to give a final concentration of 75 mg/ml was added. The system was mixed for 6 hours to allow interaction between the gellan and the nicotine.

EXAMPLE 6

Preparation of Nicotine-Alginate Complexes

A nicotine-alginate complex that can provide controlled release of nicotine in the nasal cavity can be prepared by mixing a solution of sodium alginate and nicotine dihydrogen tartrate. The concentrations of the alginate and nicotine are chosen to provide a 1:1 stoichiometric complex. The complex together with a suitable dose of free nicotine salt that will provide the pulse release phase can be administered nasally as a viscous solution or can be dried (for example by standard procedures of freeze or spray drying) and administered as a powder or a suspension. Such powder complex can be administered as the material itself or in combination with bioadhesive microspheres and powders as described by Illum et al. 1987, 1988.

4.6 g of nicotine dihydrogen tartrate (Sigma) was dispersed in 100 ml of distilled water containing 1.75 g of sodium alginate (low molecular weight grade—Protan Laboratories) by stirring over a period of 24 hours. The nicotine-alginate complex was recovered by a process of freeze drying. Other grades of alginate can also be used.

EXAMPLE 7

Preparation of Nicotine-Alginate Solution

An aqueous solution was prepared containing 20 mg/ml of sodium alginate and 51 mg/ml of nicotine dihydrogen tartrate. This concentration of nicotine salt was equivalent to 18 mg/ml of nicotine base.

Figure 2:
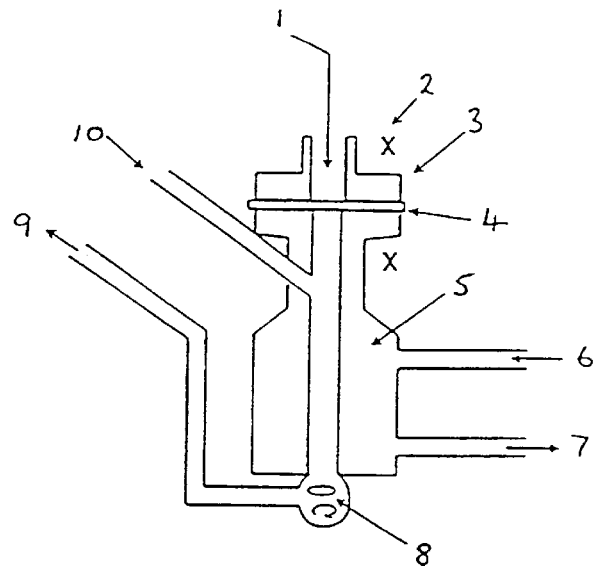
FIG. 2 is a Franz diffusion cell.
Figure 3:
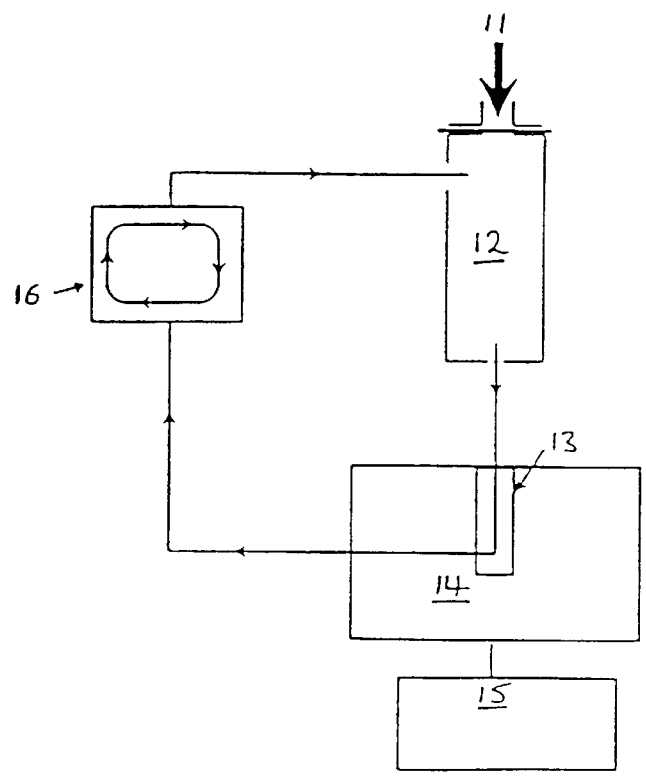
FIG. 3 is a closed loop system containing a Franz diffusion cell.

The release of nicotine from this formulations was measured using a Franz diffusion cell apparatus (see FIG. 2). The Franz-diffusion cell as shown in FIG. 2 comprises:

1—sample compartment
2—metal clasp to secure membrane
3—flange cap
4—membrane

5—water jacket
6—feed from water bath
7—exit to water bath
8—stirrer
9—eluant outlet (to cuvette)
10—eluant inlet from peristaltic pump The system in FIG. 6 comprises:

11—sample inlet
12—Franz cell
13—flow through cuvette
14—UV spectrophotometer
15—printer
16—peristaltic pump Twenty microliters of formulation (equivalent to 0.36 mg of nicotine) were applied to the membrane in the sample compartment (0.45 µm cellulose nitrate membrane). Drug diffused across the membrane into the diffusion cell which contained a stimulated nasal electrolyte solution (150 mEq/l $Na^+$, 40 mEq/l $K^+$, 8 mEq/l $Ca^{2+}$). The solution was continuously circulated through a flow cell and the appearance of nicotine monitored spectrophotometrically.

The release characteristics of the formulation indicated a biphasic profile demonstrating initial pulse release followed by a sustained release phase.

EXAMPLE 8

Preparation of Nicotine Complexed Resin

Into a 10 ml glass vial was weighed 50 mg of AMBERLITE™ IR 120 ion-exchange resin (Rohm & Haas, Philadelphia). The resin was suspended in 3.33 ml of an aqueous solution containing a total of 15.4 mg of nicotine dihydrogen tartrate (equivalent to 5 mg of nicotine base). The mixture was frozen in liquid nitrogen and lyophilised and mixed with 2 mg of (free) nicotine dihydrogen tartrate.

EXAMPLE 9

Preparation of Nicotine Complexed Resin

Into a 10 ml glass vial was weighed 50 mg of AMBERLITE™ IR 120 ion-exchange resin (Rohm & Haas, Philadelphia). The resin was suspended in 3.33 ml of an aqueous solution containing a total of 30.8 mg of nicotine dihydrogen tartrate (equivalent to 10 mg of nicotine base). The mixture was frozen in liquid nitrogen and lyophilised.

EXAMPLE 10

Preparation of Nicotine-Gel

A solution of gellan at a concentration of 0.2% w/w was prepared by dispersing 20 mg gellan gum in 1 ml of distilled water and heating to 70° C. during continuous stirring until the gellan gum was dissolved. Nicotine tartrate to give a final concentration of 3.5% was added. The system was mixed for 6 hours to allow interaction between the gellan and the nicotine.

EXAMPLE 11

It is possible to prepare combinations of microsphere materials. Into a 10 ml glass vial were weighed 50 mg of ELDEXOMER™ starch (non-carboxylated) microspheres (Perstorp, Sweden). These are non-ion-exchange microspheres. The microspheres were suspended in 3.33 ml of an aqueous solution containing a total of 15.4 mg of nicotine dihydrogen tartrate (equivalent to 5 mg of nicotine base). The mixture was frozen in liquid nitrogen and lyophilised.

The release characteristics of the lyophilised formulation were measured using the Franz diffusion cell A rapid release profile was found. One part of the ELDEXOMER™ microsphere nicotine preparation was mixed with an equal proportion of the microsphere preparation described in Example 8. The release demonstrated a pulse release of nicotine followed by a slower release phase. In this manner, by mixing microspheres of different properties, it is possible to obtain different release profiles for intended use in vivo.

Besides using in smoking cessation or as a nicotine replacement, the novel nasal delivery systems for nicotine herein described could also be useful when it is required to dose nicotine for therapeutic reasons. These include its use as a cognitive enhancer in ulcerative colitis, weight reduction, Parkinsons disease, Alzheimers disease, narcolepsy, depression, sleep apnoea.

REFERENCES

Benowitz, N. L., Pharmacological aspects of cigarette smoking and nicotine addition. N. Engl. J. Med., 319, 1318 (1988).

Benowitz, N. L., Pharmacokinetic consideration in understanding nicotine dependence, in The Biology of Nicotine Dependence, P 186, Ciba Foundation Symposium, 152, Wiley Chichester, 1990.

Henningfield, J. E. and Stilzer, M. L. (Editors) new Developments in Nicotine Delivery Systems, Cortlandt Communications, New York 1991.

Illum, L., Farraj, N. F., Critchley, H and Davis S. S., Nasal administration of gentamicin using a novel microsphere delivery system, Int. J. Pharm, 46 261 (1988).

Illum, L., Jorgensen, H., Bisgaard, H., Krogsgaard, O. and Rossing, N., Bioadhesive microspheres as a potential nasal drug delivery system, Int. J. Pharm, 39, 189 (1987).

Illum, L., and Davis, S. S., Cellulose micropsheres as a sustained release system for parenteral administration, Int. J. Pharm, 11, 323 (1982).

Johansson, C. J., Olsson, P., Bende, M., Carlsson, T. and Gunnarsson, P. O., Absolute bioavailability of nicotine applied to different nasal regions, Eur. J. Clin. Pharmacol., 41, 585 (1991).

Russell, M. A. H., Jarvis, M. J., Feyerabend, C. and Ferno, O., Nasal nicotine solution, a potential aid to giving up smoking, Br. Med. J. 286, 683 (1983).

Sutherland, G., Stapleton, J. A., Russell, M. A. H., Jarvis, M. J., Hajek, P., Belcher, M., and Feyerabend, C., Randomised controlled trial of nasal nicotine spray in smoking cessation, Lancet, 340, 324 (1992).

Codde, J. P., Burton, M. A., Kelleher, D. K., Archer, S. G., and Gray, B. N., Reduced Toxicity of Adriamycin by incorporation into ion-exchange micropheres. A therapeutic study using a rat liver. Anti cancer Res. 10 1715–1718 (1990).

Kwon, G. S., Bae, Y. H., Kim, S. W., Cremers, H and Feijen, J., Preparation and characterisation of microspheres of albumin-heparin conjugates. J. Colloid Interface Sci. 143, 501 (1991).

Sawaya, A., Benoit, J. P., and Benita, S., Binding mechanism of Doxorubicin in ion-exchange albumin microspheres. J. Pharm. Sci. 76 475 (1987).

Kwon, G. S., Bae, Y. H., Cremers, H., Feijen, J., Kim, S. W., Release of macromolecules from albumin-heparin microspheres, Int. J. Pharm., 79, 191 (1992).

Cremers, H. F. M., Feijen, J., Kwon, G., Bae, Y. H., Kim, S. W., Noteborn, H. P. J. M., McVie, J. G., Albumin-Heparin Micropheres as Carriers for Cytostatic Agents, J. Controlled Rel., 11, 167 (1990).

I claim:

1. A drug delivery composition for nasal administration comprising nicotine or a pharmacologically-acceptable compound releasing nicotine, in a formulation delivering to the nasal mucosa;

(a) an initial pulse of nicotine for rapid absorption, and (b) a controlled release of nicotine for up to twelve hours for subsequent sustained absorption, wherein the formulation comprises an ion-exchange material which forms a complex with the nicotine to provide controlled release of nicotine.

2. The composition of claim 1 wherein the formulation is in the form of microspheres.

3. The composition of claim 2 wherein the microspheres comprise materials selected from the group consisting of ionized polysaccharides and protein-polysaccharide conjugates.

4. The composition of claim 2, wherein the microspheres are formed of an ion-exchange resin.

5. The composition of claim 4 wherein the composition further comprises non ion-exchange microspheres releasing nicotine in a pulse.

6. The composition of claim 1 wherein the ion-exchange material is a polymer containing ionizable groups.

7. The composition of claim 6 wherein the ion-exchange polymer is selected from the group consisting of gellan, alginate and a mixture of alginate and gellan.

8. A method for administering nicotine to a person in need thereof comprising administering nicotine or a pharmacologically-acceptable compound releasing nicotine, in a formulation delivering to the nasal mucosa an initial pulse of nicotine for rapid absorption and a controlled release of nicotine for up to twelve hours for subsequent sustained absorption, to the nasal mucosa, wherein the formulation comprises an ion-exchange material which forms a complex with the nicotine to provide controlled release of nicotine.

9. The composition of claim 1 wherein the formulation is bioadhesive.

10. The composition of claim 1 wherein the composition contains sufficient nicotine to overload the ion-exchange material such that the excess nicotine not complexed with the ion-exchange material is delivered as a pulse.

11. The composition of claim 2 wherein the composition comprises a mixture of ion-exchange microspheres and non-ion-exchange microspheres, the non-ion-exchange microspheres providing the pulse delivery of nicotine and the ion-exchange microspheres providing the controlled release phase.

12. The composition of claim 2 which comprises nicotine or a compound releasing nicotine incorporated in non-ion-exchange bioadhesive microspheres for controlled release together with excess nicotine, which may be absorbed to the surface of the microspheres, for delivery as a pulse.

13. The composition of claim 1 wherein the ion-exchange material is an ion-exchange polymer which gels in contact with the nasal mucosa.

14. The method of claim 8 wherein the formulation is in the form of microspheres.

15. The method of claim 14 wherein the microspheres comprise polymers selected from the group consisting of ionized polysaccharides, proteins, and protein-polysaccharide conjugates.

16. The method of claim 8 wherein the formulation is in the form of microspheres and comprises ion-exchange microspheres controllably releasing nicotine and non ion-exchange microspheres releasing nicotine in a pulse.

17. The method of claim 14 wherein the microspheres are formed of an ion-exchange polymer selected from the group consisting of gellan, alginate and a mixture of alginate and gellan.

18. The method of claim 8 wherein the formulation is bioadhesive.

* * * * *